US011911516B2

(12) United States Patent
Guenzburg et al.

(10) Patent No.: US 11,911,516 B2
(45) Date of Patent: Feb. 27, 2024

(54) PROTECTION OF MICROBIAL CELLS FROM ACIDIC DEGRADATION

(71) Applicant: Austrianova Singapore Pte. Ltd., Singapore (SG)

(72) Inventors: Walter H. Guenzburg, Singapore (SG); Eva Maria Brandtner, Singapore (SG); Brian Salmons, Singapore (SG); John A. Dangerfield, Singapore (SG)

(73) Assignee: AUSTRIANOVA SINGAPORE PTE LTD., Singapore (SG)

( * ) Notice: Subject to any disclaimer, the term of this patent is extended or adjusted under 35 U.S.C. 154(b) by 140 days.

(21) Appl. No.: 17/468,481

(22) Filed: Sep. 7, 2021

(65) Prior Publication Data
US 2022/0062187 A1   Mar. 3, 2022

Related U.S. Application Data

(63) Continuation of application No. 13/981,789, filed as application No. PCT/EP2012/051132 on Jan. 25, 2012, now abandoned.

(30) Foreign Application Priority Data

Jan. 25, 2011   (EP) .................................... 11000577
Jan. 25, 2011   (EP) .................................... 11000578
Jan. 25, 2011   (EP) .................................... 11000579

(51) Int. Cl.
| | |
|---|---|
| A61K 9/50 | (2006.01) |
| A61K 35/741 | (2015.01) |
| A61K 9/48 | (2006.01) |
| A61K 35/747 | (2015.01) |
| A61K 35/742 | (2015.01) |
| A61K 36/064 | (2006.01) |
| A23L 29/00 | (2016.01) |
| A23L 29/262 | (2016.01) |
| A23P 10/30 | (2016.01) |
| A23L 33/135 | (2016.01) |

(52) U.S. Cl.
CPC ............... *A61K 9/48* (2013.01); *A23L 29/06* (2016.08); *A23L 29/262* (2016.08); *A23L 33/135* (2016.08); *A23P 10/30* (2016.08); *A61K 9/5026* (2013.01); *A61K 9/5031* (2013.01); *A61K 9/5047* (2013.01); *A61K 35/741* (2013.01); *A61K 35/742* (2013.01); *A61K 35/747* (2013.01); *A61K 36/064* (2013.01); *A23V 2002/00* (2013.01); *A23V 2400/113* (2023.08)

(58) Field of Classification Search
CPC . A61P 1/12; A61P 3/00; A23L 33/135; A61K 35/741; A61K 35/747; A61K 9/50
See application file for complete search history.

(56) References Cited

U.S. PATENT DOCUMENTS

| | | | |
|---|---|---|---|
| 5,633,012 | A | 5/1997 | Ford |
| 6,426,088 | B1 | 7/2002 | Piechaczyk et al. |
| 6,540,995 | B1 | 4/2003 | Guenzburg et al. |
| 7,122,370 | B2 | 10/2006 | Porubcan |
| 7,229,818 | B2 | 6/2007 | Porubcan |
| 2005/0266069 | A1 | 12/2005 | Simmons et al. |
| 2009/0011033 | A1 | 1/2009 | Hauser et al. |
| 2010/0215738 | A1 | 8/2010 | Ritter et al. |

FOREIGN PATENT DOCUMENTS

| | | |
|---|---|---|
| DE | 4021050 | 1/1992 |
| GB | 2135954 | 9/1984 |
| WO | WO 2006095021 | 9/2006 |
| WO | WO 2010/004018 | 1/2010 |

OTHER PUBLICATIONS

Annan et al., Encapsulation in alginate-coated gelatin microspheres improves survival of the probiotic Bifidobacterium adolescents 15703T during exposure to simulated gastro-intestinal conditions. Food Research Int. 2008;41 (2): 184-193.
Chen et al., "Preparation and characterization of NaCS-CMC/PDMDAAC capsules", Colloids and Surfaces. B, Bio Interfaces, Elsevier, Amsterdam, NL., vol. 45:3-4, Nov. 10, 2005, pp. 136-143.
Clavel et al., Survival of Bacillus cereus spores and vegetative cells in acid media simulating human stomach. J Appl Microbial. 2004;97(1):214-219.
International Search Report and Written Opinion issued in PCT/EP2012/051132 dated Jun. 1, 2012.
Corcoran et al. Survival of Probiotic Lactobacilli in Acidic Environments is Enhanced in the Presence of Metabolizable Sugars. (Year: 2005).
Dautzenberg et al., Methods for a comprehensive characterization of microcapsules based on polyelectrolyte complexes. Biomater Artif Cells Immobilization Biotechnol. 1993;21 (3):399-405.

(Continued)

*Primary Examiner* — Robert T. Crow
*Assistant Examiner* — John P Nguyen
(74) *Attorney, Agent, or Firm* — KNOBBE, MARTENS, OLSON & BEAR LLP

(57) ABSTRACT

A simple cellulose sulphate based microencapsulation technology has been applied to encapsulate bacterial or other microbial cells, which produce and release digestive enzymes and thereby provides an acid resistant shelter for these microbial cells. Surprisingly, the resulting spheres were found to provide sufficient protection for encapsulated cells from treatment with aqueous acidic solutions. Thereby the cellulose sulphate microencapsulated cells, such as probiotics are now enabled to survive passage, for example, through the stomach after consumption by a human or animal with a higher survival rate than those not within a microcapsule. After passing the stomach these cells are delivering products produced by them, e.g. enzymes or other nutrition factors. This technology therefore proves to be very useful in providing digestive or otherwise beneficial enzymes and/or of living microbial cells, into the lower gastrointestinal tract, where they could confer their health benefit to the host.

12 Claims, 3 Drawing Sheets

(56) References Cited

OTHER PUBLICATIONS

Dautzenberg et al., Preparation and Performance of Symplex Capsules. Makromol Chem., 1985;Suppl. 9:203-210.

Dautzenberg et al., Size exclusion properties of polyelectrolyte complex microcapsules prepared from sodium cellulose sulphate and poly[diallyldimethylammonium chloride]. J Membrane Sci. 1999;162(1-2):165-171.

Horst Dautzenberg et al., "Development of Cellulose Sulfate-based Polyelectrolyte Complex Microcapsules for Medical Applications", Annals of the New York Academy of Sciences, vol. 875:1 Bioartificial, Jun. 1, 1999, pp. 46-63.

Islam etal., Microencapsulation of live Probiotic Bacteria. J Microbial Biotechnol. Oct. 2010;20{10):1367-1377.

Kailasapathy, Microencapsulation of Probiotic Bacteria: Technology and Potential Applications. Curr Issues Intest Microbial. Sep. 2002;3(2):39-48.

Khater et al., Effect of Encapsulation on some Probiotic Criteria. J Am Sci. 2010;6(10):810-819.

Marteau et al., Survival of Lactic Acid Bacteria in a Dynamic Model of the Stomach and Small Intestine: Validation and the Effects of Bile. J Dairy Sci. Jun. 1997; 80(6):1031-37.

Merten et al., A new method for the encapsulation of mammalian cells. Cytotechnology. Oct. 1991; 7{2):121-130.

Nazzaro et al., Fermentative ability of alginate-prebiotic encapsulated Lactobacillus acidophilus and survival under simulated gastrointestinal conditions. J Functional Foods 2009;1(3):319-323.

Pelegrin et al., Immunotherapy of Viral Disease by in Vivo Production of Therapeutic Monoclonal Antibodies. Hum Gene Ther. Jul. 1, 2000;11(10):1407-1415.

Porubcan, Survival Probiotics. CEO, Master Supplements, dated Mar. 9, 2009, accessed online at: http:/fwww.survivalprobiotics.com/randy_commentary.html {last seen on Nov. 15, 2010).

Sul Tana et al., Encapsulation of probiotic microbial cells with alginate-starch and evaluation of survival in simulated gastrointestinal conditions and in yoghurt. Int J Food Microbial. Dec. 5, 2000;62(1-2):47-55.

Truelstrup-Hansen et al., Survival of Ca-alginate microencapsulated *Bifidobacterium* spp. in milk and simulated gastrointestinal conditions. Food Microbiol. 2002; 19:35-45.

Ye et al. Cultivation of Lactobacillus in Microcapsules. Pub Med. 2000.

Zhang et al. Preparation of Macroporous Sodium Cellulose Sulphate/ polydimethyldiallylammonium chloride Capsules and Their Characteristics. Journal of Membrane Science. vol. 255, Issues 102, Jun. 2005.

Zhang et al., Preparation of macroporous sodium cellulose sulphate/ poly (dimethyldiallylammonium chloride) capsules and their characteristics. J Membrane Sci. 2005;255{1-2):89-98.

Sodium cellulose sulphate (NaCS)

Poly(diallyldimethylammonium chloride) (pDADMAC)

PROTECTION OF MICROBIAL CELLS FROM ACIDIC DEGRADATION

RELATED APPLICATIONS

The present invention is a continuation application of U.S. patent application Ser. No. 13/981,789, filed Oct. 8, 2013, which was filed under 35 U.S.C. § 371 as the U.S. national phase of International Application No. PCT/EP2012/051132, filed Jan. 25, 2012, which designated the U.S. and claims the benefit of priority to European Patent Application Number 11000579.0, filed Jan. 25, 2011, and to European Patent Application Number 11000577.4, filed Jan. 25, 2011, and to European Patent Application Number 11000578.2, filed Jan. 25, 2011, each of which is hereby incorporated in its entirety including all tables, figures, and claims.

FIELD

The invention refers to a (simple) cellulose sulphate based microencapsulation technology which has been applied to encapsulate bacterial or other microbial cells which produce and release digestive enzymes and thereby provides an acid resistant shelter for these microbial cells. Surprisingly, the resulting spheres were found to provide sufficient protection for encapsulated cells from treatment with aqueous acidic solutions. Thereby the cellulose sulphate microencapsulated cells, such as probiotics are now enabled to survive passage, for example, through the stomach after consumption by a human or animal with a higher survival rate than those not within a microcapsule. After passing the stomach, these cells are delivering products produced by them, e.g. enzymes or other nutrition factors. This technology therefore proves to be very useful in providing digestive or otherwise beneficial enzymes and/or of living microbial cells, into the lower gastrointestinal tract, where they could confer their health benefit to the host. Described is how cells are encapsulated with said material, and under which conditions the encapsulated cells survive the stomach passage and how the microbial cells or enzyme produced by said microbial cells can exit the microcapsules allowing the cells and/or the enzymes produced within the microcapsules to provide their health benefit. This technology will play an important role in the improvement of food, especially probiotic foods or the delivery of food additives to improve human and animal health and wherein these cells are still able to release their generated products e.g. enzymes and/or other nutritional factors into the surrounding environment after having been exposed to an acidic environment first.

BACKGROUND

Digestive Enzymes

Digestive enzymes are enzymes that break down polymeric macromolecules (such as contained in food) into their smaller building blocks (such as nutrients and waste products), in order to facilitate their absorption by the body. Digestive enzymes are found in the digestive tract of animals, which in the context of the present invention can be any, but preferably mammals, especially ruminants and other livestock, aquatic farmed animals such as fish and shrimp, pets and companion animals, avians and/or humans, where they aid in the digestion of food as well as inside the cells, especially in their lysosomes where they function to maintain cellular survival. Digestive enzymes are diverse and are found in the saliva secreted by the salivary glands, in the stomach secreted by cells lining the stomach, in the pancreatic juice secreted by pancreatic exocrine cells, and in the intestinal (small and large) secretions, or as part of the lining of the gastrointestinal tract. Digestive enzymes are classified based on their target substrates: Proteases and peptidases cleave proteins into their monomers, the amino acids; lipases split fat into three fatty acids and a glycerol molecule; carbohydrases cleave carbohydrates such as starch into sugars; nucleases split nucleic acids into nucleotides.

In the human digestive system, the main sites of digestion are the oral cavity, the stomach, and the small intestine. Digestive enzymes are secreted by different exocrine glands including: salivary glands, secretory cells in the stomach, secretory cells in the pancreas, secretory glands in the small intestine. The pancreas produces digestive enzymes, such as lipases, amylases and proteases that act in the small intestine. Known proteases are trypsin, chromotrypsin and carboxypeptidase.

The full benefit of food and nutritional supplements are only gained if the body has enough enzymes to properly digest the food and absorb the nutrients. Some digestive enzymes are found only in raw foods which are not routinely eaten and are not part of the usual diet most animal take in. Digestive enzymes produced by the animal's body, might become less abundant with the age of the animal; the older the animal, the less its body produces of them. A lack of digestive enzymes can contribute to a myriad of illnesses including arthritis, obesity, irritable bowel syndrome, heartburn, chronic fatigue syndrome and more. A lack of proteases can cause incomplete digestion that can lead to allergies and the formation of toxins.

It is commonly believed that taking supplements to increase levels of digestive enzymes would improve the body's ability to access and use food nutrients for energy, cell growth, and repair. By improving one's digestion supplements will often reduce gas and heartburn, and improve regularity. An estimated 15% of Americans suffer from arthritis, which is usually characterized with adjectives for inflammation such as; pain, swelling, stiffness, and redness. However, arthritis is not a single disorder, but the name of joint disease from a number of possible causes, such as genetics, infections, physical injury, allergies, stress, and faulty digestion. Clinical work at the Transformation Enzyme Corporation revealed that most arthritis sufferers respond well to treatment with protease and digestive enzyme supplements because arthritis is related to inflammation and digestion. Several studies have shown protease enzymes to be as effective as the drugs Methotrexate and Indomethacin for arthritis pain relief, but without the negative side-effects. By increasing support of the digestive and immune systems, inflammation is reduced.

A solution to health problems related to a lack of digestive enzymes is to take digestive enzyme supplements orally. Most digestive enzymes come in capsules which you can simply swallow. Capsules are made either of gelatin (called gel capsules) or vegetable cellulose blend (called veggie capsules). Most supplement companies have been moving toward veggie capsules over the past 10 years for all their encapsulated supplements. Most enzyme capsules can be opened and the powder poured out.

Simply swallowing additional amounts of digestive enzymes might not be the ideal solution, because the exposure to stomach acid when passing through the stomach might have a detrimental effect to the enzymes. Additional problems in providing enzymes as a food supplement are the taste of such enzymes, some of them cause a "burning sensation" in the mouth, and their sensitivity towards moisture. Non-encapsulated enzymes have been reported to lose their potency when they are exposed to normal air humidity, they therefore also cannot be taken as a drink or be taken as ingredient of a moist meal, unless added just before consumption.

The burning sensation is caused when proteases start to breakdown some of the dead layer or cells on the skin surface. These enzymes do remove damaged, infected, or dead cells. If proteases linger on the skin surface for a prolonged period, they may remove the dead cells exposing the healthy skin below. This can lead to irritation. Sometimes if enzymes are taken in a drink, which gets to the upper lip, proteases can linger and can cause a rash there.

Then there are also digestive enzymes that are sensitive to stomach acid. Pancreatic enzymes are not stable at wide ranges in pH or temperature and are destroyed by stomach acid. Thus, they need to be protected during passage through the stomach.

Probiotics

One of the fastest growing segments in both the human and animal health industries is the use of probiotic cells (probiotics). According to the currently adopted definition by FAO/WHO, probiotics are: "Live microorganisms which when administered in adequate amounts confer a health benefit on the host". Lactic acid bacteria (LAB, Lb.) and bifido bacteria are the most common types of microbes used as probiotics; but certain yeasts and bacilli may also be helpful.

Probiotic microbial cells are sensitive to various environmental conditions such as pH, moisture, temperature, air and light. When these conditions are not properly controlled, the product's viability (often measured in colony forming units (cfu), or as metabolic activity rates (mar)), and therefore its efficacy, can be substantially reduced.

To be used as beneficial, potentially even therapeutic compounds in a diet, the probiotic microbial cells need to be protected a) during the manufacturing process, and b) during storage within the product and c) while passing through the digestive tract, especially the stomach. In dairy products such as yoghurts they have to survive mildly acidic conditions for an extended period of time. Probiotic survival in products is affected by a range of factors including pH, post-acidification (during storage) in fermented products, hydrogen peroxide production, oxygen toxicity (oxygen permeation through packaging), storage temperatures, stability in dried or frozen form, poor growth in milk, lack of proteases to break down milk protein to simpler nitrogenous substances and compatibility with traditional starter culture during fermentation. All these stresses result in death of a significant percentage of these cells. Therefore International Dairy Federation (IDF) suggests that a minimum of $10^7$ probiotic microbial cells should be alive at the time of consumption per gram of the product, in order to achieve the acclaimed health benefits. It is believed however that this number can be decreased significantly when the major cause of cell death, i.e. the acidic degradation of the living cells in the stomach can be avoided by protecting the cells from such an acidic environment and thereby increasing the survival rate of cells in the stomach. A number of probiotic microbial cells are also able to produce digestive enzymes as well as when passing through the stomach and entering the intestine.

Microencapsulation

One solution to the problem of poor survival of probiotic microbial cells for example during storage in fermented dairy products or during exposure to stomach acid is microencapsulation. Encapsulation is the process of forming a continuous coating around an inner matrix that is wholly contained within the capsule wall as a core of encapsulated material. It must be distinguished from "immobilisation" which refers to the trapping of material within or throughout a matrix. In contrast to encapsulation, this is a random process resulting in undefined particle size where a percentage of immobilised elements will be exposed at the surface. Microencapsulation helps to separate a core material from its environment, thereby improving its stability and extending the core's shelf life. The structure formed by the microencapsulation agent around the core substance is known as the wall. The properties of the wall system are designed to protect the core and to potentially release it under specific conditions while allowing small molecules to pass in and out of the membrane. The capsules may range from submicron to several millimetres in size and can be of different shapes.

Several food grade biopolymers such as alginate, starch, xanthan gum, guar gum, locust bean gum and carrageenan gum as well as whey proteins have been tested as microencapsulation materials to protect the acid sensitive microbial cells with varying successes. For a recent review see Islam et al. "Microencapsulation of Live Probiotic Bacteria" J. Microbiol. Biotechnol. (2010), 20(10), 1367-1377. So far nobody reported on the use of a microencapsulation technology that allows digestive enzymes that are produced inside of microbial cells, to be released through the capsule wall.

Alginates

Alginates are natural anionic polysaccharides made up by D-mannuronic and L-guluronic acid residues joined linearly by 1-4 glycosidic linkages. Alginate is a natural product recovered from seaweed, which is considered to be non-toxic and alginate encapsulation is a widely used technology, due to its simple preparation and low price and good biocompatibility (the material does not affect the viability of most types of encapsulated cells). Alginate gels made from $Ca^{2+}$ alginate are stable in low pH. They swell in weakly basic solutions. When the pH is lowered below the pKa values of D-mannuronic and L-guluronic acid, though, alginate is converted to alginic acid with release of $Ca^{2+}$ and the formation of a more dense gel due to water loss.

An article by Kaila Kailasapathy ("Microencapsulation of Probiotic Bacteria: Technology and Potential Applications", Curr. Issues Intest. Microbiol. (2002), 3, 39-48) provides a good overview of the different microencapsulation techniques that had been used up to that time.

It was reported that about 40% more lactobacilli survived freezing of ice milk when they were entrapped in calcium alginate than when they were not entrapped. An aqueous solution of alginate or carrageenan in vegetable oil containing Tween 80 (emulsifier) and sodium lauryl sulphate (surfactant) was used to encapsulate probiotic bacterial cells. The bacterial cells were mixed in a solution of alginate and dropped into oil to accomplish encapsulation. The emulsifier and surfactant were added to promote capsule formation.

Some of these micro-encapsulation laboratory procedures involve water-in-oil emulsion technology. This technique however may not be suitable for all food product applications because, firstly, the residual oil in the encapsulated material may be detrimental to texture and organoleptic characteristics, and may not be suitable for the development of low-fat dairy products. Secondly, the residual oil, emulsifier and surfactant in the encapsulated material can be toxic to live microbial cells and may interact with sensitive food components.

Also a modified alginate-starch encapsulation method has been described, wherein the prebiotic Hi-maize starch was incorporated during the calcium-alginate microencapsulation of probiotic cells. Cells encapsulated in presence of this starch had a prolonged shelf-life, compared to those encapsulated without the starch. Prebiotics are non-digestible food ingredients that stimulate the growth and/or activity of microbial cells in the digestive system which are beneficial to the health of the body. Typically, prebiotics are carbohydrates (such as oligosaccharides), but the definition may include non-carbohydrates, they are non digestible by the host organism (such as a mammal or human), but provide benefits to the microorganisms that can digest them. However, the encapsulated microbial cells did not show a significantly increased survival rate when subjected to low pH and high bile salt conditions during in vitro tests. They were exposed to conditions of pH 2, 3 or 4 for 3 hrs at 37° C. and samples were taken hourly. It turned out that Lactobacillus acidophilus is more sensitive than Bifidobacterium, but that the encapsulation did not protect the microbial cells from being degraded by aqueous acidic solutions (Sultana et al. "Encapsulation of probiotic microbial cells with alginate-starch and evaluation of survival in simulated gastrointestinal conditions and in yoghurt", International Journal of Food Microbiology, (2000), 62(1-2), 47-55).

However, probiotics must not only be able to survive the manufacturing and storage conditions of food but must also eventually be fit to enter the gut. Therefore, they also have to survive gastric acidity, bile salts, enzymes, toxic metabolites, bacteriophages, antibiotics and anaerobic conditions, before they can exert their beneficial effect in the intestine.

Conventionally generated alginate capsules with diameters of 40-80 micrometer have been reported to confer only an insignificant protection of bifidobacteria when exposed to simulated gastric juice at pH 2.0 while larger alginate (1-3 mm) microspheres protected the encapsulated cells more substantially (Truelstrup-Hansen L, Allan-wojtas P M, Jin Y L, Paulson A T, "Survival of free and calcium-alginate microencapsulated Bifidobacterium spp. in simulated gastro-intestinal conditions.", Food Microbiol. (2002), 19: 35-45).

In 2009 Nazzaro et al. encapsulated L. acidophilus bacteria in alginate-inulin-xanthan gum and reported significantly enhanced cell viability after fermentation and storage ($6\times10^{12}$ and $4\times10^{10}$ cell s/ml versus $4\times10^{10}$ and $2\times10^{8}$ for free cells, respectively) as well as improved survival rates in simulated gastric acid (Nazzaro, F. et al., "Fermentative ability of alginate-prebiotic encapsulated Lactobacillus acidophilus and survival under simulated gastrointestinal conditions", Journal of Functional Foods (2009), 1(3), 319-323).

Also lately, a novel microencapsulation method based on gelatin microspheres which are cross-linked with the non-cytotoxic genipin and coated with alginate cross-linked by $Ca^{2+}$ from external and internal sources, was described. The encapsulation in alginate-coated gelatin microspheres significantly ($P<0.05$) improved the survival of probiotic Bifidobacterium during exposure to adverse environmental conditions. Cell survival after exposure to simulated gastric juice, pH 2.0, for 5 min was only 2% and 1% of the initial populations for uncoated gelatin microspheres and free cells respectively. However, 54% and 20% of the initial populations survived when the bacteria were in alginate-coated microspheres produced by external and internal $Ca^{2+}$-sources, respectively. After the initial losses (5 min) though, the populations of bifidobacteria declined at the same rate for all treatments over the 2 h incubation period. The decrease in the viable population by 3.45 log units for free B. adolescentis cells was similar to findings by others who observed reductions of about 3 log cfu ml for B. adolescentis exposed to Simulated gastric juice (SGJ, pH 2.0) for 2 to 3 h. (Annan N. T., Borza A. D. and Truelstrup Hansen L., "Encapsulation in alginate-coated gelatin microspheres improves survival of the probiotic Bifidobacterium adolescentis 15703T during exposure to simulated gastro-intestinal conditions", Food Research international, (2008), 41(2), 184-193).

The time between start of their journey to the lower intestinal tract via the mouth, and release from the stomach has been reported to be about 90 min. Therefore, when Khater et al. compared the survival rates of 12 different probiotic strains encapsulated with alginate—encapsulation was performed according to a modified version of Sultana's protocol (as described above involving the Hi-maize starch)—under acidic stress, treatment times of 30, 60 and 90 mins in acidified medium were used (Khater & Ahmed, "Effect of Encapsulation on some Probiotic Criteria", Journal of American Science, (2010), 6 (10), 810-819). Cellular stress begins in the stomach, which has a pH value as low as 1.5. In most in vitro assays however pH 3.0 is used to test acid resistance. The alginate encapsulated cells were therefore compared to non-encapsulated cells at a pH of 2 and a pH of 3. All non-encapsulated strains were strongly affected at pH 2.0, whereas alginate encapsulated bacteria survived a little bit longer in pH 2.0. The overall survival rates, however, were higher at pH 3.0 also for the encapsulated cells indicating that the effects of acidic stress cannot completely be prevented.

Furthermore, Khater et al. compared survival rates of these alginate encapsulated and non-encapsulated strains after exposure to different concentrations of bile salt, and also tested the effect of simulated gastric juice (SGJ at pH of 1.4) on viability of these bacteria. When the exposure times were increased to 24 hrs at pH 3.0 plus 12 hrs in a 0.3% concentrated oxgall solution, the results confirm that under these conditions alginate encapsulation increases the survival rate of probiotic bacteria in low pH followed by a treatment with bile salt. For one strain the survival rate after the 36 hrs treatment increased from 17% to 34% and for another strain from 37% to 50%. Survival rates between capsulated and non-encapsulated cells differed by only approximately 2% after an exposure of 3 hrs in the simulated gastric juice conditions though, a treatment apparently less detrimental for all cell strains, as survival rates even of non-encapsulated cells remained between 89% and 92% in this experiment.

However, in contrast, it has been reported that none of the free cells of Lactobacillus bulgaricus KFRI 673 survived a 60 min period in simulated gastric fluid (SGF) at pH 2.0, whereas the cells did survive a period of two hours in simulated intestinal fluid (SIF), suggesting that L. bulgaricus KFRI 673 is pH-sensitive and cannot survive in acidic pH conditions (reviewed by Islam, see above). Furthermore, Porubcan reported that about 99% of the viability of free cells is lost after they have been exposed to the stomach. His experiments show that exposure to simulated gastric acid at pH 1.6 for a period of 90 min dramatically reduces the viability of all cultures tested (U.S. Pat. No. 7,122,370, Example 1).

The U.S. Pat. Nos. 7,122,370 and 7,229,818 of Porubcan describe an acid induced encapsulation with alginate, which is resistant to low pH conditions. The formulation used includes a substantially water free mixture of probiotic cells with sodium or potassium alginate salts. The mixture has been formed and is maintained in an essentially water-free environment, by encoating the alginate/bacteria mix with an enteric coating, for example a capsule made of cellulose or gelatin. This "macro"-capsule is meant to protect the mixture of bacterial cells and alginate salts from becoming moist. Hence basically the solid cellulose capsule is providing an enteric coating protecting the two component mix until the capsule is dissolved in the stomach, where acid resistant microcapsules will then form, made of alginic acid and probiotic bacteria as soon as they get in contact with the acidic environment in the stomach. Due to the acid induced formation of the microcapsules, the probiotic bacterial cells seem to be protected from the gastric juice in the stomach while being encapsulated. Porubcan claims that cellulose as excipient, which is disclosed to encapsulate the mixture of alginate and cells and to provide a formulation that can easily be swallowed, is not protective with regards to the gastric acid in the stomach (http://www.survivalprobiotics.com/randy_commentary.html (last seen on 15 Nov. 2010):

"The probiotic bacteria are grown in the tanks in a broth medium for about 18 hours and then harvested by centrifuge and freeze-dried. The freeze-dried powders are filled into capsules along with food grade excipients such as cellulose. The big problem with this process is that it yields products with poor shelf-life (even when refrigerated) and poor survival in the stomach—all the CFU, literally 99.99%, get killed by stomach acid."

While this system provides one solution to provide viable probiotics to customers, it is however not suitable for all uses as a food ingredient, as it is generating rather large capsules, which need to be swallowed intact, and may not be bitten open.

Already in 1995 a patent application was filed which discloses various methods of microencapsulation for lactobacilli and suggests to orally administer microencapsulated probiotic lactobacilli within pharmaceutically acceptable capsules, such as gelatine capsules, to prevent antibiotic associated diarrhoea—wherein the microencapsulation is described as a means to extend the bacterial shelf life, and to protect the bacteria from degradation while passing through the gut (U.S. Pat. No. 5,633,012). Described are microencapsulation systems using sodium alginate alone or alginate and poly L-lysine. One system is described wherein the bacteria are mixed with hydroxypropylmethylcellulose to be added into a solution of a mix of freely water permeable and partially water permeable acrylic methacrylic acid ester copolymers in acetone-isopropanol. The cellulose derivative serves as a carrier only, and is not part of the capsule. Two other microencapsulation processes described in here involve the use of polyvinylpyrrolidone or polyvinylpovidone.

The abandoned patent application US 2005/0266069 A1 by Simmons is another comprehensive source of information on the state of the art concerning the different methods of preparing stable probiotic microsphere compositions. Herein, a rather complex probiotic microsphere is described comprising a core of probiotic bacteria, a cellulosic excipient, a disintegrant and an additive, as well as an enteric coating resistant of gastric fluids. The enteric coating capable of being resistant to gastric fluids is comprised of a polymer or copolymer of acrylic acid and/or methacrylic acid and/or their esters, cellulose acetate phthalate, polyvinyl acetate phthatlate and shellac.

Concerning the methods of producing such capsules there are generally two different approaches. Simmons describes a technique involving the extrusion of polymer solutions, followed by spheronization which may comprise a series of non-continuous stages known as granulation (to form an extrudable paste), extrusion, spheronization and drying, followed by another step of coating said microspheres.

This rather complex production method is in contrast to the much simpler technique, which is employed for the generation of cellulose sulphate microencapsulated probiotics, according to the present invention. The latter simply involves two steps of dispersing the cells in the cellulose sulphate solution and introducing the mixture for example in form of droplets into a hardening solution, also referred to as precipitation bath. Basically preformed spherically droplets which are charged and therefore don't stick together fall into a hardening solution.

Cellulose Sulphate Microcapsules

In a different field, i.e. in the area of biomedicine and healthcare applications, living cells are encapsulated with the aim to inject them inside the body of a patient (i.e. implant them), where they are expected to deliver therapeutic biomolecules, substrates or enzymes which then pass through the membrane of the microcapsule, which protects them from being attacked by the body's immune system and localises them.

An alternative technology to the use of alginate described above, i.e. the forming of polyelectrolyte complex (PEC) microcapsules by oppositely charged polyions is a simple and effective method. The commonly employed polyelectrolyte capsule systems are sodium cellulose sulphate (herein referred to as NaCS)/poly[diallyl(dimethyl)ammonium chloride] (herein referred to as pDADMAC), chitosan/alginate, chitosan/xanthan, etc. pDADMAC is a quaternary ammonium homopolymer. The CAS name of pDADMAC is 2-Propen-1-aminium,N,N-dimethyl-N-Propenyl-,chloride homopolymer. It can be purchased at different molecular weights.

The NaCS/pDADMAC encapsulation system formed by dropping a solution of polyanion NaCS into a solution of polycation pDADMAC, has been systematically investigated and it captivates by its simplicity thereby decreasing the costs of the process and eliminating potential sources of contaminants. Molecules like nutrients and waste products can easily pass through the cellulose sulphate microcapsule pores, if the capsules have been made with comparatively small pDADMAC molecules. The material is biocompatible and long term survival could be documented for some cell types which were encapsulated with this system. It was characterized and optimized for biomedical purposes, and the microcapsules have subsequently been applied successfully, for example in the field of tumour therapy where the encapsulated living cells produce therapeutic compounds such as antibodies, which are released through the capsule pores within the patient's body (U.S. Pat. No. 6,540,995 to Gunzburg et al. and U.S. Pat. No. 6,426,088 to Piechaczyk et al.).

First experiments performed in house were showing that acidic protons $H_3O^+$ would easily pass through the cellulose sulphate capsule walls. When $CaCO_3$ particles were encapsulated with sodium cellulose sulphate and small sized pDADMAC they completely dissolved when an aqueous acidic solution was added. The dissolving is happening in a time dependent manner. FIG. 2 is showing pictures of such capsules embedding $CaCO_3$ crystals which are dissolved slowly, at a pH below 6, in a time dependent manner. When reducing the pH further from pH 7.5 to pH 3 the $CO_2$ generated is forming bubbles within the capsules.

Therefore, it is surprising that NaCS/pDADMAC capsules are able to protect microbial cells from the effect of an acidic environment.

The idea to use this NaCS/pDADMAC system based encapsulation technology in order to protect the microbial cells from degradation through gastric juice in the stomach, and further while passing through the intestine was tested herein and, surprisingly, the microbial cells inside the macroporous capsules made of cellulose sulphate and pDADMAC (FIG. 3) survived the acid treatment much longer than the non-encapsulated cells (FIG. 4), despite of the capsules' rather large pore size (demonstrated in U.S. Pat. Nos. 6,540,995 and 6,426,088 to allow the release of macromolecules) and the teaching in the art that cellulose as excipient does not protect the cells from degradation through gastric juice in the stomach. Furthermore the cells remained viable and metabolically active. Most of the cells then still remained encapsulated while being treated with intestinal fluids, such as duodenal juice, hence the cells are enabled to pass through the digestive tract, for example, including the intestine, within the microcapsules and to thereby release the enzymes they produce, through the capsule pores into their surrounding environment. Depending on the microencapsulation conditions a release of microencapsulated microbial cells in the gut can be adjusted in order to improve the release of microbial cells from the microcapsules.

SUMMARY

This invention is about the use of a specific microencapsulating material and methods to protect living microbial cells, which might be bacteria and other microorganism like fungi or yeast, in particular probiotic cells, which is a heterologous group consisting of special yeast, special fungis and special bacteria, from acidic degradation in acidic aqueous solution and further enable them to pass through the digestive tract, while remaining viable. It is also about the encapsulation of microbial cells which release enzymes, through the capsule pores into their surrounding environment, after having survived acidic gastric juice of animals, which might be vertebrates, but preferably avians and mammals, to gain the according health benefit. It is to be understood that the invention as described throughout the entire document can be applied to different other subgroups of animals as well. However, preferred animals are avians, especially avians which are useful for food production like geese, chicken, turkeys, fish, shrimp or mammals, like rodents, dogs or cats, but especially mammals which are useful for food production like ruminants (cattle, goats, sheep, bison, moose, elk, buffalo, deer) or pigs. Most preferred are however, humans in order to prevent or to treat gastrointestinal imbalances. Macroporous cellulose sulphate capsules containing microbial cells, such as microbial cells producing digestive enzymes and especially probiotics are provided which are resistant to a treatment with HCl acidified aqueous solution, especially with gastric acid or gastric fluid, for an extended time of at least 1 h and which are further resistant to treatment with intestinal fluids, such as simulated intestinal fluid (SIF) or duodenal juice, etc. The process to microencapsulate the microbial cells is surprisingly simple. The experimental data provided here reveal that the microencapsulation of microbial cells with sodium cellulose sulphate (NaCS) and poly[diallyl-dimethyl-ammonium chloride] (pDADMAC) resulted in macroporous microcapsules which protect the encapsulated microbial cells successfully from degradation in an acid environment, as well as in the rather basic environment of intestinal juices (pH is essentially around 8). Even after 90 mins of treatment with HCl at pH 2.0 the metabolic activity of the encapsulated microbial cells is still high compared to non-encapsulated cells. This is surprising because hydrogen ions ($H_3O^+$) are expected to rapidly diffuse into the capsule due to the relatively large pore size (of about 80 kDA or higher), as has been shown in studies demonstrating that cellulose sulphate encapsulated cells do allow passage of substances as large as antibodies through their pores in the capsule wall. For some reason the encapsulation with sodium cellulose sulphate and pDADMAC resulting in macroporous capsule surfaces nevertheless provides a significant protection from degradation with acidic solutions. When treated with intestinal fluids such as duodenal juice the microcapsules still remain intact. The pore size is however large enough to allow the enzymes secreted by the microbial cells to pass through the capsule wall and be released, for example, into the digestive tract. This enables the passage of a high number of viable, metabolically active e.g. probiotic cells through the stomach into the intestine.

The cell microencapsulation technology, which is based on the use of sodium cellulose sulphate, which can be either homogenously or heterogenously sulphated cellulose, and pDADMAC has so far not been applied in order to protect the encapsulated bacteria or probiotics from acidic degradation, nor from degradation through extended periods of storage or both.

It is one embodiment of the invention to provide this technology for use in the food industry. Encapsulated microbial cells are especially useful to enhance weight gain in farm animals. Substitution e.g. of intrinsic microbial populations by microbial strains providing a more effective enzyme composition lead to an enhanced food utilisation. Therefore, the use of the technology and microcapsules as described above in the food industry is another embodiment of the invention.

By originating from a chemically defined starting material, surrounding the cells with such a cellulose based PEC capsule, which is not only of high mechanical strength and good biocompatibility, but also unaffected by acidic conditions, and able to respond to a change in the surrounding environment by releasing the cells and/or cell products from the capsules when passing through the intestine, a solution to the problem of the poor survival of the majority of cells, such as probiotics in dietary products and in orally administered food additives is achieved.

BRIEF DESCRIPTION OF THE FIGURES

FIG. 1A represents the chemical structure of sodium cellulose sulphate (NaCS).

FIG. 1B represents the chemical structure of the Poly [diallyl-dimethyl-ammonium chloride] (pDADMAC).

Figure 1A:
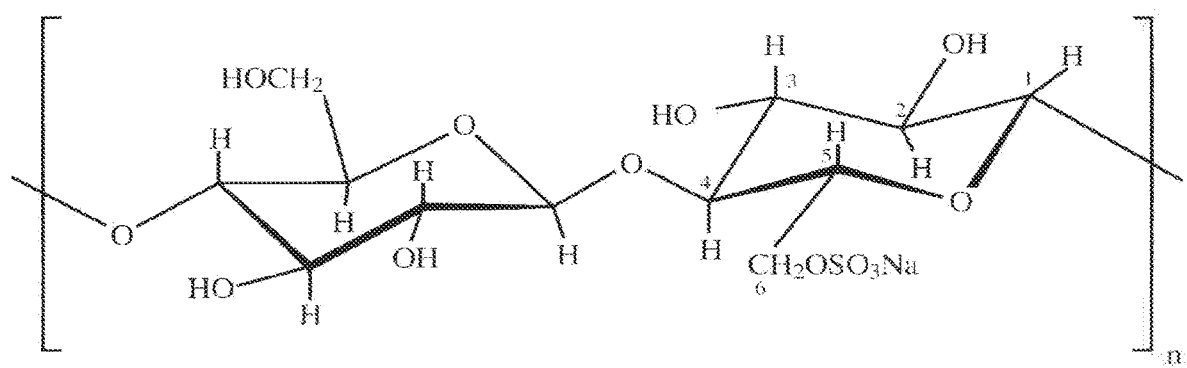
FIGS. 1A and 1B represent the chemical structure of the polyelectrolytes used for encapsulation.

*dophilus* in acidic conditions (HCl, pH2) for a period of up to 4 hours. The viability was determined by Alamar Blue® assay and measured in relative fluorescence units (RFU).

DETAILED DESCRIPTION

The subject of the invention is encapsulated microbial cells, comprising capsules having a porous capsule wall, wherein the porous capsule wall comprises a complex formed from cellulose sulphate and poly[dimethyldiallyl-ammonium chloride], which are characterized as being resistant to treatment with acidic aqueous solution, especially bacterial cells that are sensitive to treatment with acidic aqueous solution, when not encapsulated. The cell microencapsulation technology used herein is based on the use of sodium cellulose sulphate which may be produced either by homogenously or heterogeneously sulphated cellulose. The pDADMAC used in the methods according to the invention is of a rather small molecular weight, as has been described by Dautzenberg et al. (1999b). (Dautzenberg H, Schuldt U, Grasnick G, Karle P, Müller P, Löhr M, Pelegrin M, Piechaczyk M, Rombs K V, Günzburg, W H, Salmons B, Saller R M.

"Development of cellulose sulfate-based polyelectrolyte complex microcapsules for medical applications". *Ann. N.Y. Acad. Sci.* (1999), 875, 46-63). Here it was disclosed that the optimum mechanical strength of the capsule wall can be achieved with pDADMAC of about 20 kDa. The capsules produced that way are characterised as having pores large enough to allow passage of proteins or monoclonal antibodies, according to a size of at least 80 kDa or even up to 150 kDa. The dependency of pore size and the size of the pDADMAC used has been disclosed by Dautzenberg et al. (1999a) ("Size exclusion properties of polyelectrolyte complex microcapsules prepared from sodium cellulose sulphate and pDADMAC", Journal of Membrane Science, (1999), 162(1-2), 165-171). It is clear that a lower molecular weight of the pDADMAC results in a lager pore size. It is preferred that the microcapsules having pore sizes large enough to allow the release of enzymes from microbial cells which are producing and excreting digestive enzymes.

In one embodiment of the invention the capsules are having the form of spheric microcapsules with a diameter of between 0.01 and 5 mm, preferably between 0.05 and 3 mm and most preferably between 0.01 and 1 mm. It is also preferred that the capsules have a porous capsule wall, which is permeable to said digestive enzymes. The microcapsules are characterized as to comprise surface pores which allow the enzymes to pass through. It is preferred that the surface pore size of the porous capsule wall is between 80 and 150 nm, to allow the enzymes to pass. It is especially preferred that the surface pores of the porous capsule wall have a molecular weight cut off (MWCO) between 50 and 200 kDa, preferably between 60-150 kDa and most preferably between 60 and 100 kDa.

Examples of the digestive enzymes and their sizes are proteases, such as Subtilisin from B. *Subtilis*, with a size of about 27 kDa, alpha-amylases of about 63 kDA, alpha-galactosidases of about 82 kDa, bromelain proteases of about 25 kDA, cellulases of about 32 kDa, glucoamylases of about 78 kDa, pectinases of about 35 kDa and lipases from *Bacillus subtilis* of about 20 kDa in size. The exact size might vary from organism to organism. Some of these enzymes also act as dimers. It is preferred that the cells are cells which are beneficial to an animal according to the present invention after consumption. It is preferred that the cells are selected from the group comprising yeasts such as *Saccharomyces, Debaromyces, Candida, Pichia* and *Torulopsis*, fungi such as *Aspergillus, Rhizopus, Mucor*, and *Penicillium* and *Torulopsis* and bacteria such as *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Geobacillus* and probacteria such as *Lactobacillus*. In the context of the present invention microbial cells might be selected from the groups comprising yeast, fungi and bacteria and/or probiotics or as a further embodiment of the present invention microbial cells might be combined from those groups. In the context of the present invention the term probiotics or probiotic cells is used interchangeably. It is preferred that these encapsulated microbial cells, especially those that secret digestive enzymes are selected from the group containing *Saccharomyces, Bifidobacterium, Lactobacillus, Enterococcus, Streptococcus, Bacillus, Lactococcus, Leuconostoc, Pediococcus, Propionibacterium* and *Geobacillus*.

More preferably the cells are selected from a group comprising *Saccharomyces cereviseae, Bacillus coagulans, Bacillus licheniformis, Bacillus subtilis, Bifidobacterium angulatum, Bifidobacterium animalis, Bifidobacterium bifidum, Bifidobacterium breve, Bifidobacterium infantis, Bifidobacterium lactis, Bifidobacterium longum, Enterococcus faecium, Enterococcus faecalis, Lactobacillus acidophilus, Lactobacillus amylovorus, Lactobacillus alimentarius, Lactobacillus bulgaricus, Lactobacillus casei* subsp. *casei, Lactobacillus casei Shirota, Lactobacillus curvatus, Lactobacillus delbrueckii* subsp. *lactis, Lactobacillus fermentum, Lactobacillus farciminus, Lactobacillus gasseri, Lactobacillus helveticus, Lactobacillus johnsonii, Lactobacillus lacti, Lactobacillus paracasei, Lactobacillus pentosaceus, Lactobacillus plantarum, Lactobacillus reuteri, Lactobacillus rhamnosus (Lactobacillus GG), Lactobacillus sake, Lactobacillus salivarius, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus*, and *Staphylococcus xylosus*.

It is especially preferred that the cells are probiotic cells. It is especially preferred that the probiotic cells are selected from the group comprising *Lactobacillus acidophilus, Lactobacillus caseei, Lactobacillus delbrueckii* sub sp *bulgaricus, Lactobacillus johnsonii, Lactococcus lactis* subsp *lactis, Lactococcus lactis* subsp *cremoris, Streptococcus thermophilus, Bifidobacterium bifidum, Bifidobacterium angulatum* and *Bifidobacterium longum*. In one specific embodiment the cells are *Lactobacillus acidophilus* or *Bacillus subtilis* cells.

Encapsulated *Lactobacillus acidophilus* cells, comprising capsules having a porous capsule wall, wherein the porous capsule wall comprises a complex formed from either homogenously or heterogeneously sulphated cellulose sulphate and poly[dimethyldiallyl-ammonium chloride] thereby providing that these encapsulated cells are resistant to a treatment with acidic aqueous solution of a pH value of 2 for a time period of 2 to 4 hours are therefore a specific embodiment of the invention. It is a preferred embodiment wherein the cells are resistant for a time period of 2 hours.

It may be understood that the term "resistant" comprises a situation, wherein a majority of microbial cells is still viable after such treatment.

It is preferred that a majority of these cells is still viable after such a treatment with an acidic aqueous solution. It is especially preferred that the majority of cells is still metabolically active after such treatment and that the cells still produce and release enzymes. In this context the majority is understood to be at least 51% of the cells. It is preferred that 60% to 90% of the cells remain viable. It is even more preferred that 60% to 80% of the cells remain viable. It is an especially preferred embodiment wherein 60% of the cells remain viable after acidic treatment.

It is understood that at least more of the encapsulated cells are metabolically active after treatment with an acidic aqueous solution, than cells of the same type that were not encapsulated and treated under the same conditions.

It is a preferred embodiment wherein the time of treatment with acidic aqueous solution is between 0.5 and 2.5 hrs, preferably between 1 and 2 hrs, and most preferably 1.5 hrs. It is also a preferred embodiment of the present invention wherein the acidic aqueous solution has a pH range between 1.0 and 3.0, preferably between 1.5 and 2.5, most preferably is a pH of 2.0.

It is a preferred embodiment that the encapsulated cells according to the invention produce and release digestive enzymes, which are selected from the group comprising amylases, such as alpha-amylases, galactosidases, especially alpha-galactosidases, proteases, especially bromelain protease and subtilisin, cellulases, hemicellulases, pectinases and lipases. It is preferred that the enzymes are selected from the group containing the above. It is especially preferred that the encapsulated cells are selected from the group of *Bifidobacterium, Lactobacillus, Enterococcus, Streptococcus, Bacillus, Lactococcus, Leuconostoc, Pediococcus, Propionibacterium* and *Geobacillus*.

In a preferred embodiment of this invention the microbial cells are *Bacillus subtilis* cells and the secreted enzymes are proteases, especially subtilisin. Another embodiment of the invention related to encapsulated probiotic cells, comprises capsules having a porous capsule wall, wherein the porous capsule wall comprises a polyelectrolyte complex formed from the counter-charged polyelectrolytes cellulose sulphate and poly[dimethyldiallyl-ammonium chlorid], thereby providing that these encapsulated probiotic cells are resistant to treatment with acidic aqueous solution, and wherein the capsules are characterised as to release at least a part of the living probiotic cells upon treatment with intestinal fluids. The acidic aqueous solution may be gastric juice or gastric fluid. The treatment with intestinal fluid comprises passing through the intestine of an avian or of a mammal, including a human. Preferably the intestinal fluid comprises duodenal juice or fluid. It is a preferred embodiment that the encapsulated probiotic cells, comprising capsules as described above are characterised as surviving a treatment with simulated gastric fluid (SGF), and wherein a treatment with simulated duodenal fluid or simulated intestinal fluids (SIF) triggers or causes the release of at least a part of the probiotic cells out of the capsules.

Another embodiment of the present invention is to provide a food supplement comprising such encapsulated microbial cells, according to the different embodiments as described above, is also understood to be an embodiment of the invention. Furthermore a formulation, preferably a pharmaceutical formulation or pharmaceutical composition comprising encapsulated microbial cells, preferably probiotic bacterial cells, or encapsulated yeasts or encapsulated fungal cells, which are preferably probiotic fungal cells as described above is another embodiment of the invention. The encapsulated microbial cells may be used as a medicament or preventing agent. They may be used to treat or prevent diarrhea, including diarrhea caused by antibiotics and other forms of suffering from an unbalanced bacterial population in the intestine, be it in response to an antibiotic treatment or not.

The sodium cellulose sulphate used in the methods according to the invention was produced by the homogenously sulphating method starting with cellulose linters. However, it is also possible to use heterogenously sulphated cellulose, as also this material according to Dautzenberg et al. (1999b)("Development of Cellulose Sulphate-based Polyelectrolyte Complex Microcapsules for Medical Applications", Ann. N.Y. Acad. Sci., (1999), 875, 46-63.) results in the formation of capsules with large pores, of at least 80 kDa.

A food supplement comprising such encapsulated microbial cells or encapsulated probiotics is also understood to be an embodiment of the invention. Furthermore a formulation, preferably a pharmaceutical formulation comprising encapsulated bacterial cells or probiotics, as described above is another embodiment of the invention.

In WO/2006/095021 (US 20090011033) a method has been described, that describes the production of cellulose sulphate of sufficient quality. It is preferred that the cellulose sulphate used is of a molecular weight of between 100-500 kDa, preferably 200-400 kDa, and most preferably between 250-350 kDa. The experiments in the Example section of the present application were performed with NaCS material (09-Sul-592) provided by the Fraunhofer Institute of Applied Polymer Research (IAP) in Potsdam, Germany.

The preparation of cellulose sulphate capsules has been thoroughly described in DE 40 21 050 A1 of Dautzenberg. Also the synthesis of the cellulose sulphate has been described therein, methods for a comprehensive characterization of cellulose sulphate capsules have been extensively dealt with in H. Dautzenberg et al., Biomat. Art. Cells & Immob. Biotech., (1993), 21(3), 399-405. Other cellulose sulphate capsules have been described in GB 2 135 954. The properties of the cellulose capsules, i.e. the size, the pore size, wall thickness and mechanical properties depend upon several factors such as for example physical circumstances whereunder the capsules have been prepared, viscosity of precipitation bath, its ion strength, temperature, rapidity of addition of cell/cellulose sulphate suspension, constitution of cellulose sulphate, as well as other parameters described by the Dautzenberg group.

Generally, in order to form the capsules the sodium cellulose sulphate is brought in contact with an aqueous pDADMAC solution, which may be purchased e.g. from Aldrich Co., USA or Katpol Chemie to name a few. Alternatively, poly[dimethyldiallyl-ammonium chloride] (pDADMAC or also referred to as PDMDAAC) may be prepared via radical polymerization of dimethyl-diallyl-ammonium chloride, (according to the University of Potsdam, Department of Chemistry, Teltow, Germany). Mansfeld and Dautzenberg suggest to use a 1.2% (w/v) solution of PDMDAAC (pDADMAC) in destilled water. pDADMAC may be purchased in a variety of different sizes. Zhang et al. (Zhang, Yao and Guan, 2005 Preparation of macroporous sodium cellulose sulphate/poly(dimethyldiallylammonium chloride) capsules and their characteristics. Journal of Membrane Science. Volume 255, Issues 1-2, 2005, Pages 89-98) used a pDADMAC with a molecular weight of 200,000-350,000 Da, whereas Dautzenberg suggests a pDADMAC of a molecular weight of 10,000-30,000 Da.

In WO/2006/095021 (US 20090011033) a method has been described, that results in cellulose sulphate samples of sufficient quality. In this process a reaction mixture of n-propanol and sulphuric acid served as sulphating medium and agent.

Figure 1B:
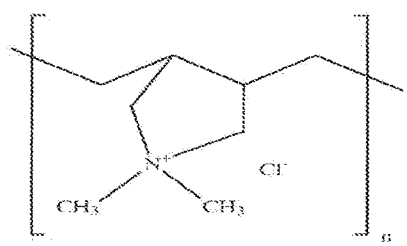
Figure 2:
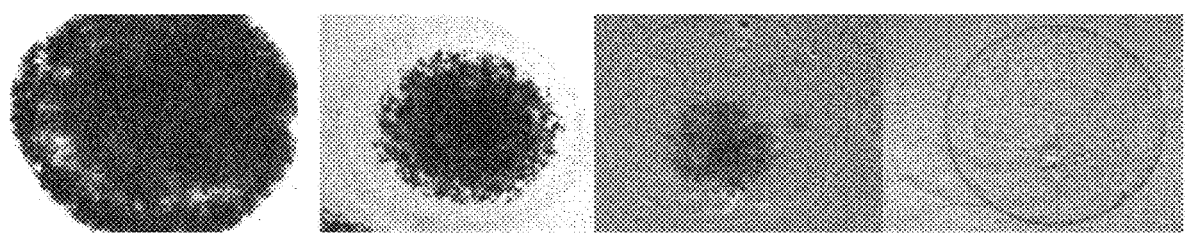
FIG. 2 is showing a series of pictures representing capsules made of cellulose sulphate and pDADMAC according to the invention, which contain $CaCO_3$ at different pH values. The first capsules are at a pH of 7.5 and contain $CaCO_3$ crystals. The last picture shows the capsules at a pH of 3, wherein the $CaCO_3$ crystals are dissolved and bubbles of $CO_2$ are visible inside the capsules. This demonstrates that acid ($H_3O^+$) can freely enter the capsules and dissolve the $CaCO_3$ crystals. Therefore, it is very surprising that the NaCS/pDADMAC capsules are able to protect microbial cells from the effect of an acidic environment.
Figure 3:
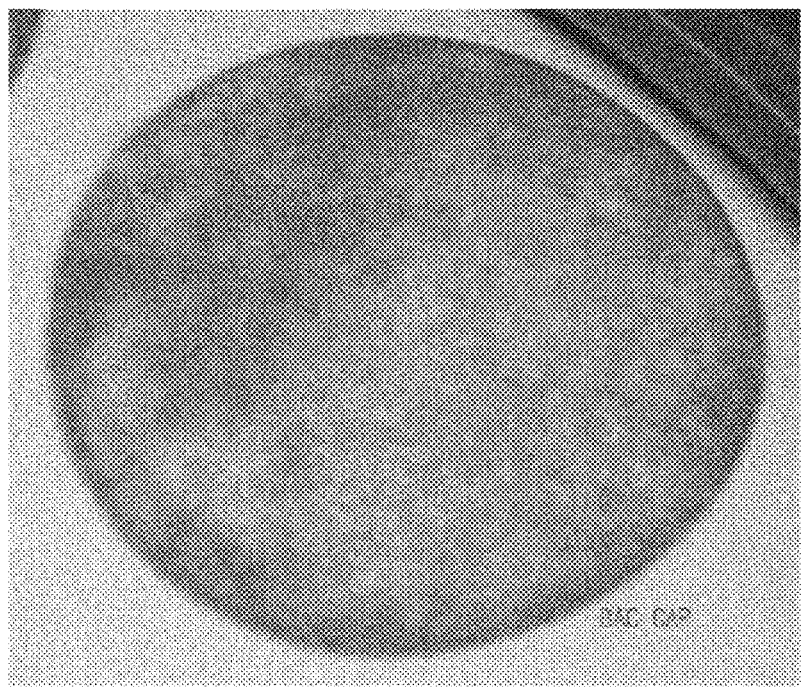
FIG. 3 shows a light microscopic picture of NaCS/pDADMAC encapsulated *Lactobacillus acidophilus* cells.

Sodium cellulose sulphate (FIG. 1A) serves as polyanion and poly[diallyldimethylammonium chloride] (pDADMAC) (FIG. 1B) as polycation. The NaCS solution is used to build the capsule core and the pDADMAC solution as a precipitation bath delivering the second reaction component for PEC formation at the surface of the droplets, thus forming the capsules by covering the droplets with a solid membrane. A commercially available encapsulating machine may be used to form microcapsules, which in the context of the entire invention are also referred to as beads or microspheres. Such an encapsulator includes a perfussor drive which pushes a NaCS solution with defined velocity through a nozzle and thus generates a continuous liquid flow. The liquid flow is forced to oscillate by a pulsation unit, where the superimposed oscillation causes the break-off of the outlet liquid stream or jet into beads of equal volume. In order to improve the mono-dispersibility of the beads and at the same time to reduce coalescence, an electric field is provided under the nozzle outlet in such an encapsulator. Electrostatic charging in the free phase causes a repulsion of the individual beads, so that an aggregation of the individual beads up to entry into the complex-forming bath is substantially prevented.

The spheric beads formed in this manner are dropped into a complex-forming bath, within which at the outer membrane of the capsule is formed around the capsule by electrostatic interaction, for example between the NaCS and a pDADMAC solution. Under constant stirring, the capsules remain in this system until reaching a desired hardening degree in the corresponding container and are then available for further processing.

In lack of an encapsulator or other airjet droplet generator system, a syringe can be used with a 0.2 to 1.0 mm inner diameter needle possibly with a suitable syringe pump extrusion system. Alternatively the use of a pasteur pipette with e.g. an inner diameter of 1.5 mm also works to generate acid resistant capsules according to the present invention.

The resulting capsules have a pore size large enough to allow macromolecules up to 80 kDa or even up to 150 kDa, e.g. antibody proteins to pass. Capsules produced that way have been reported to have pore sizes large enough to release antibodies through these pores which are produced from hybridoma cells within these capsules. The cellulose sulphate encapsulation technology described by Dautzenberg et al. 1999b ("Development of Cellulose Sulphate-based Polyelectrolyte Complex Microcapsules for Medical Applications") was employed to test whether in vivo production of a neutralising monoclonal antibody could protect mice against Fr-CasE retrovirus (Pelegrin et al., "Immunotherapy of Viral Disease by in Vivo Production of Therapeutic Monoclonal Antibodies", Human Gene Therapy (2000), 11, 1407-1415). From these results it is clear that the capsules have pores large enough to allow a monoclonal antibody to pass through.

It is understood however that substances and methods of the invention are not limited to the use of the specific ingredients described herein; instead the invention comprises also the use of ingredients purchased from other sources or ingredients, produced by methods such as described above.

Before encapsulation the microbial cells are best grown to an OD 600 nm of 1 and harvested. However, other OD 600 are suitable as a starting point as well. Then they are encapsulated with cellulose sulphate and pDADMAC as follows:

Microbial cells are microencapsulated with NaCS according to the method of Dautzenberg et al. ("Preparation and Performance of Symplex Capsules", Makromol. Chem., Suppl. 9, 203-210, 1985; "A new method for the encapsulation of mammalian cells", Merten et al., Cytotechnology 7:121-120, 1991; "Development of Cellulose Sulphate-based Polyelectrolyte Complex Microcapsules for Medical Applications" Annals of the New York Academy of Sciences, 875 (Bioartificial Organs II: Technology, Medicine, and Materials), 46-63, 1999b). Briefly, NaCS serves as polyanion and builds the capsule core. Poly[diallyldimethylammonium chloride] solution as polycation provides a precipitation bath delivering the second reaction component for the polyelectrolyte complex formation at the surface of the cellulose sulphate capsule core, thus forming microcapsules by covering the NaCS core droplets with a solid membrane.

The microbial cultures are grown up to an optical density indicating that they are in a fully viable state, for most of the microbial cells this might be best an optical density of 1. Then a portion, for example 50 ul, 100 ul, or 200 ul of the bacterial culture is mixed with about 20 times (100 ul are mixed with 2 ml) of that volume of sodium cellulose sulphate solution containing 1.8% sodium cellulose sulphate (09-5 ul-592, Fraunhofer Institute Golm, Germany) and 0.9% to 1% sodium chloride. Small amounts of that solution, for example droplets are then introduced into a bath of 1.3% 24 kDa (21-25 kDa average size) pDADMAC. This may be done with the use of a syringe and a needle, if no encapsulator is available or with the droplet generator system as described above. After a hardening time of 4 mins and several wash steps, the encapsulated cells are obtained from the bath and ready for use or storage.

These encapsulated cells may now additionally as a further embodiment of the invention be added to different types of food as food ingredients. Alternatively they may be consumed as a pharmaceutical composition, or pharmaceutical formulation. For example, they may be provided as (macro-)capsules with an enteric coating, which makes it suitable to swallow the right amounts of microcapsules to achieve the desired health benefit, such as in addition to supporting intestinal health and function, include (depending on the bacterial strain selected) repopulating the gut after antibiotic therapy, offsetting lactose intolerance, supporting the immune system and reducing cholesterol. Nutritional benefits include their role in enhancing the bio-availability of calcium, zinc, iron, manganese, copper and phosphorus and synthesis of vitamins. The therapeutic benefits of these microbial cells include antimicrobial activity, ability to assimilate cholesterol, improved lactose intolerance and anti-carcinogenic activity.

After encapsulation the encapsulated microbial cells might be further cultivated until the entire capsule volume is filled with microbial cells, which can be seen as a dense mass in the microscope. The more dense the capsules are filled with microbial cells, the more they are protected from the acidic environment and the more microbial cells survive the stomach passage or an incubation with acid aqueous solutions or gastric fluid.

It is therefore another embodiment of the invention to provide a method to protect cells from being degraded by treatment with an acidic aqueous solution, by encapsulation comprising a) suspending the living cells in an aqueous solution of a polyelectrolyte sodium cellulose sulphate, b) introducing the suspension in form of preformed particles into a precipitation bath containing an aqueous solution of the counter-charged polyelectrolyte poly[dimethyldiallylammonium chloride], c) terminating the reaction in the bath after 1 to 60 mins, preferably 3-10 mins, more preferably 3-5 mins and most preferably after 4 mins, d) harvesting the encapsulated cells from the bath, e) optionally incubating the encapsulated cells in a medium or solution comprising further nutritional factors, f) optionally incubating the encapsulated cells until the capsules are filled entirely with cells, g) exposing the encapsulated cells to treatment with an acidic aqueous solution, which is known to degrade said cells, if they are not encapsulated, whereby the majority of encapsulated cells remains viable. In this context the majority is understood to be at least 51% of the cells, at least 60% or between 60 and 90% of the cells. In a preferred embodiment between 60% and 80% of the cells remain viable.

It is a preferred embodiment of the invention, wherein the method as claimed provides protection from acidic treatment with aqueous solution for a period of between 0.5 and 3 hours. In a preferred embodiment the period is between 1 and 2 hrs, and especially preferred is a period of 90 mins. Herein it is understood that protection is achieved if either a majority of cells is still viable or is still metabolically active or if more of the encapsulated cells remain viable when compared with unencapsulated cells which are treated under the same conditions. Metabolically active is understood as showing a reading on a UV-Vis spectrophotometer at 570 nm after incubation with resazurin which is reduced to fluorescent resorufin that is significantly different from the background or a negative control value.

Furthermore it is preferred that the acidic aqueous solution the cells are treated with is either gastric juice, gastric fluid or simulated gastric fluid or simulated gastric juice. The exposure to treatment with acidic solution may be an incubation in acidic aqueous solution, and it is a preferred embodiment wherein said treatment is performed under physiological conditions. Furthermore, it is preferred that the encapsulated cells are further resistant to being treated with intestinal fluids, such as simulated intestinal fluid, or duodenal juice.

The term "simulated gastric fluid" is understood to comprise different artificially prepared gastric fluids that have been disclosed in the literature. One of them is described here as an example: The simulated gastric fluid may for example be prepared on the basic gastric fluid and the pepsin. The basic gastric fluid has been prepared according to Clavel et al. (J Appl Microbiol. (2004), 97(1), 214-219) with some modifications. It contained 4.8 g of NaCl (POCH, Poland), 1.56 g of $NaHCO_3$(POCH, Poland), 2.2 g of KCl (POCH, Poland), and 0.22 g of $CaCl_2$) (POCH, Poland) dissolved in 1 L of distilled water. After the autoclaving at 121° C./15 min, the pH of the basic gastric fluid was adjusted to 2.4±0.2 using 1 M HCl, and 2 mg of pepsin (Sigma Aldrich, USA) per 50 mL of the artificial gastric fluid was added.

The term "simulated intestinal fluid" is understood to comprise different artificially prepared intestinal or duodenal fluids that have been disclosed in the literature. One of them is described here as an example: The simulated duodenal fluid may be prepared on the basic duodenal fluid and an enzyme complex. The basic duodenal fluid may be prepared according to Marteau et al. (J Dairy Sci. 1997: 80(6), 1031-37) with some modifications. It contained 5.0 g of NaCl (POCH, Poland), 0.6 g of KCl (POCH, Poland), 0.03 g of $CaCl_2$) (POCH, Poland), and 17 g of bile salts (Merck, Germany) dissolved in 1 L of 1 mol/L $NaHCO_3$ (POCH, Poland). After the autoclaving at 121° C./15 min, the pH of the basic juice was adjusted to 7.0±0.2 using 1 M NaOH, and an enzyme complex was added. The enzyme complex comprised of pancreatin enzymes: 20000 F.I.P. units of lipases, 16000 F.I.P. units of amylases, 1200 F.I.P. units of protease (=2 capsules of Kreon® 10000 (300 mg pancreatin enzymes) purchased from Solvay Pharmaceuticals, USA) were added per 50 mL of fluid.

It is another embodiment of the invention to provide a method of producing encapsulated microbial cells which generate and excrete digestive enzymes, with sodium cellulose sulphate and pDADMAC, resulting in microcapsules containing microbial cells, that are resistant to treatment with aqueous acidic solutions and that have a porous wall allowing the generated enzymes to pass through, comprising the following steps
  i) suspending a culture of such microbial cells with a sodium cellulose sulphate solution, preferably containing 1.8% sodium cellulose sulphate and 0.9 to 1% sodium chloride,
  ii) introducing the suspension in form of preformed particles into a precipitation bath preferably comprising 1.3% 24 kDa (20-25 kDa) pDADMAC, and harvesting microcapsules containing microbial cells from the bath. It is preferred that the reaction in the precipitation bath is terminated after 1-60 mins, preferably 1-10 mins, more preferably 3-5 mins, and most preferably after 4 mins for example by adding an excessive amount of washing solution.

A further embodiment of the invention comprises a method to prevent acidic degradation of probiotic microbial cells by encapsulation with sodium cellulose sulphate and pDADMAC, comprising the following steps suspending a culture of probiotic cells with a sodium cellulose sulphate solution containing 1.8% sodium cellulose sulphate and 0.9%-1% sodium chloride, introducing the suspension in form of preformed particles, for example by using a 5 ml syringe and a 23 G needle into a precipitation bath comprising 1.3% 24 kDa pDADMAC, wherein 24 kDa pDADMAC is to be understood as the average size, and harvesting microcapsules containing probiotic cells from the bath. It is a preferred embodiment wherein the reaction in the precipitation bath is terminated after 3-5 mins, preferably after 4 mins. 24 kDa pDADMAC from supplier Katpol Chemie is specified to embrace a range of 20-25 kDa.

For microencapsulation of *L. acidophilus* cells, the cells obtained from the culture may be mixed with NaCS as described and microcapsules may be produced manually with a syringe and a needle, as described in the example.

Further the invention provides for a method to introduce viable cells, which are sensitive to gastric acid if unencapsulated, into the intestine of animals, including humans, comprising administering encapsulated cells as have been described above.

It is also provided for a method to treat or prevent diarrhea, antibiotic caused diarrhea and other forms of suffering from an unbalanced bacterial population in the intestine by administering encapsulated cells according to the invention to mammals suffering or expected to suffer from said diarrhea, antibiotic caused diarrhea and other forms of suffering from an unbalanced bacterial population in the intestine.

The skilled reader will be aware that the cell density, as well as the concentrations of the NaCl may be varied. Also the forming of capsules is not limited to the exact hardening time of 240 s. Moreover, the NaCl solution may be replaced by a PBS solution or other buffer solutions.

The size of the capsules can be varied from 200-1200 µm in diameter, if produced in an automated process involving an apparatus such as the encapsulator IE-50R and IEM-40 from EncapBioSystems, Switzerland, previously distributed by Inotech. It is a preferred embodiment of the invention wherein the capsule size is 200-700 µm, and even more preferred wherein the capsule size is 200-500 µm.

An alternative production method involves the use of Pasteur pipettes. When using pasteur pipettes for production of capsules manually the diameter of the microcapsules reached a size of 3,000-5,000 µm.

A large sized capsule thereby clearly requires a different mode of uptake by an informed consumer, or patient, who is aware that he needs to swallow the dietary supplement without chewing it first, in order to allow full protection from stomach acid of the cells in the intact microcapsules. The size should otherwise not affect the survival times during processing and storage.

It is a preferred embodiment of the invention that the size of the capsules is between 500 and 700 µm in diameter.

It is another preferred embodiment that the capsules have a diameter of at least 3,000 um when manually prepared, i.e. without an apparatus such as an encapsulator.

The so encapsulated cells may be used as additives to food, in cases where the encapsulated cells are meant to survive the stomach acid treatment. They may also be stored for prolonged periods of time at room temperature (RT).

A formulation, such as a pharmaceutical formulation comprising encapsulated microbial cells according to the method described above is another embodiment of the invention.

The application of these new substances and methods as described throughout, such as the encapsulated microbial cells resistant to acidic fluids, for the farming industry is also an embodiment of the invention. Due to similarities with the human digestion system the methods and substances of the invention can be used for delivery of beneficial probiotics to animals, especially humans in order to reduce gut associated problems by increasing feed digestion, nutrient absorption. In connection with farming purposes the delivery of beneficial probiotics can be used to increase meat production. It is to be understood that the invention as described throughout the entire document can be applied to different subgroups of animals like avians, especially avians which are useful for food production like geese, chicken, turkeys, fish, shrimp or of mammals which are useful for food production like ruminants (cattle, goats, sheep, bison, moose, elk, buffalo, deer).

Herein above is provided a method for preparing encapsulated microbial cells which produce and excrete digestive enzymes, wherein these capsules have a porous capsule wall, which is permeable to said digestive enzymes and are resistant to treatment with aqueous acidic solutions. That method comprises suspending the cells, which produce digestive enzymes, in an aqueous solution of polyelectrolyte, whereafter the suspension in the form of preformed particles, such as drops, is introduced into a precipitation bath containing an aqueous solution of a counter-charged polyelectrolyte.

EXAMPLES

In the following examples an Assay has been employed to measure the metabolic activity of cells, which is named AlamarBlue® assay. "AlamarBlue" is a registered trademark name by TREK Diagnostic Systems for an assay that is provided e.g. by Invitrogen or Promega. In the following the name AlamarBlue will be used to refer to an assay which uses the active ingredient natural reducing power of living cells to convert resazurin, a cell permeable compound that is blue in colour and virtually non-fluorescent. Upon entering metabolically active cells resazurin, the non-fluorescent indicator dye, is reduced to bright red-fluorescent resorufin. The amount of fluorescence produced is proportional to the number of living cells. 10 ul of AlamarBlue® was added into 100 ul of cell suspension and incubated for 2 hrs at 37° C. The fluorescence of the AlamarBlue® assay plate was read with a Tecan Infinite M200 reader. The fluorescence may be detected with any plate reader or fluorescence spectrophotometer using 560EX nm/590EM nm filter settings. Alternatively, the absorbance of AlamarBlue® can be read on a UV-Vis spectrophotometer at 570 nm.

The microbial cells and probiotics used for encapsulation were delivered freeze dried from the according supplier, and then cultivated in liquid medium. Samples of these cultures were kept frozen as glycerol stocks for use in separate experiments.

Example 1: Growing of *Lactobacillus acidophilus* to an OD of 1.0

A culture of *Lactobacillus acidophilus* was started with a 20 ul sample from the thawed bacteria stock by injecting it into 50 ml MRS (named by its inventors: de Man, Rogosa and Sharpe, developed in 1960; Preparation of 1 liter of MRS medium: 51 g MRS broth powder, 1 g Polysorbate 80, 0.5 g L-cysteine hydrochloride and 999 ml of $H_2O$ adjusted to pH of 6.2.) in a 50 ml EM flask. The stock had been kept at −80° C. and was purchased from DSM (catalogue number DSM 20079) (Moro) Hansen and Mocquot (ATCC 4356). The culture was incubated overnight shaking at 50 rpm and at 37° C. On Day 1 of the experiment, the optical density of the bacterial culture was determined at 600 nm on Tecan Infinite M200. Typically the optical density at 600 nm that gives a reading of 1 will correspond to the exponential phase of the bacterial growth. The cells were grown up to an OD 600 nm reading of 1, to ensure that cells were in the exponential phase before performing the stress tests (see Table 1).

TABLE 1

*Lactobacillus acidophilus* culture profile growing overnight

| | | Growing Time in hrs | OD600 |
|---|---|---|---|
| Day 0 | 4 pm | 0 | n.a. |
| Day 1 | 9 am | 17 | 0.5805 |
| Day 2 | 2 pm | 22 | 1.0012 |

Example 2: Survival of Non-Encapsulated *Lactobacillus acidophilus* Cells in Hydrochloric Acid A solution of 0.01M HCl in PBS (phosphate buffered saline) was prepared by adding 4.2 ml of 37% HCl to 500 ml PBS. The pH value was adjusted to 2.0 exactly by using 5M HCl.

5 ul of the *lactobacillus* culture was added to 1 ml of hydrochloric acid in PBS (phosphate buffered saline salt solution) in a sterile Eppendorf tube in triplicate. As a control, 5 ul of the same *Lactobacillus* culture was added to 1 ml of PBS in a sterile Eppendorf tube in triplicate at 0 hr time point. The hydrochloric acid testing was carried out at different time points, i.e. after 1 hr, 1.5 hr and 2 hrs of exposure time.

At the various time points all the Eppendorf tubes were centrifuged down at speed of 3000×g for 1 min to remove hydrochloric acid. They were washed twice with MRS medium and 100 ul of MRS medium was added into the pellet. The pellet was resuspended therein and all was transferred into a 96 well plate.

An AlamarBlue assay, as described above, was carried out to determine the metabolic activities of the bacteria cells.

TABLE 2

Viability of free *Lactobacillus acidophilus* determined as AlamarBlue readings in RFU after different exposure times to HCl

|  | Blank Reading | 0 h | 1 h | 1.5 h | 2 h |
|---|---|---|---|---|---|
|  | 3013 | 33073 | 26915 | 17932 | 3412 |
|  | 3023 | 32348 | 26695 | 23011 | 3362 |
|  | 3209 | 33877 | 11176 | 15657 | 4484 |
| Mean | 3082 | 33099 | 21595 | 18867 | 3753 |
| Corrected Reading |  | 30018 | 18514 | 15785 | 671 |

Example 3: Encapsulation of *Lactobacillus acidophilus* Cells in NaCS and pDADMAC 100 ul of the bacteria culture with an optical density of 1 were mixed with 2 ml of sodium cellulose sulphate solution containing 1.8% sodium cellulose sulphate (09-5 ul-592, provided by the Fraunhofer Institute) and 1% sodium chloride, and dropped into a 150 ml bath of 1.3% 24 kDa pDADMAC with the use of a 5 ml syringe and a 23 G needle.

The hardening time for the capsules in the pDADMAC bath was 4 mins. The capsules were then washed once for 8 min with 300 ml of 1×PBS, and once 4 mins with 300 ml of 1×PBS. These were followed by 3 washes with 30 ml 1×Phosphate Buffered Saline each and 3 washes with 30 ml MRS medium each. The capsules were then transferred to a 250 ml conical flask containing 100 ml of fresh MRS medium. These capsules were cultured at 37° C. incubator, with a speed of 50 rpm.

The AlamarBlue Assay described above was performed on the encapsulated *lactobacillus* cells. The assay was performed in triplicate on a Blank (100 ul LB medium+10 ul alamar-blue) and on the capsules (100 ul MRS medium+ 10 ul Alamar-Blue). The samples comprising the suspended cells and the indicator dye were incubated for 2 hrs in the plate at 37° C., and then measured.

TABLE 3

Viability of encapsulated *Lactobacillus acidophilus* determined as AlamarBlue readings in RFU at day 2 post encapsulation

|  | Blank | Reading |
|---|---|---|
|  |  | 25726 |
|  |  | 24916 |
|  |  | 19246 |
| Mean | 3432 | 23296 |
| Corrected Reading |  | 19864 |

Example 4: Survival of Encapsulated *Lactobacillus acidophilus* in Hydrochloric Acid After having confirmed that the capsules are viable, hydrochloric acid testing was performed on the *lactobacillus* capsules. 1 capsule to 1 ml of hydrochloric acid in Phosphate Buffered Saline was placed in each well of a 24 well plate at different time points, at 4 hrs, 3 hrs, 2 hrs and 1 hr in triplicate. As a control to the experiment, 1 capsule was added to 1 ml Phosphate Buffered Saline at 0 h time point in triplicate.

At 0 h, the hydrochloric acid phosphate buffered saline solution was replaced with MRS medium. The capsules were washed twice with MRS media and then transferred 1 by 1 to a 96 well plate. 100 ul of fresh MRS medium and 10 ul alamar blue were added and incubated for 2 hrs. AlamarBlue assay plate was read on Tecan Infinite M200.

TABLE 4

Viability of encapsulated lactobacilli determined by AlamarBlue readings in RFU after different exposure times to HCl

|  | Blank | 0 h | 1 h | 2 h | 3 h | 4 h |
|---|---|---|---|---|---|---|
|  | 3298 | 25627 | 30832 | 16041 | 21733 | 24908 |
|  | 3429 | 24755 | 29182 | 18070 | 26421 | 19157 |
|  | 3491 | 26126 | 30969 | 18248 | 23770 | 19961 |
| Mean | 3406 | 25503 | 30328 | 17453 | 23975 | 21342 |
| Blanked Samples |  | 22097 | 26922 | 14047 | 20569 | 17936 |

A comparison of the AlamarBlue readings of *lactobacillus* free bacteria and encapsulated bacteria after HCl testing shows that after 2 hrs in HCl the viability of free bacteria dropped drastically indicating that free bacteria don't survive an exposure time of 2 hrs in HCl. The RFU readings of encapsulated bacteria however remain high even after 4 hrs of exposure to HCl indicating a higher viability and improved survival in capsules in HCl environment.

Figure 4:
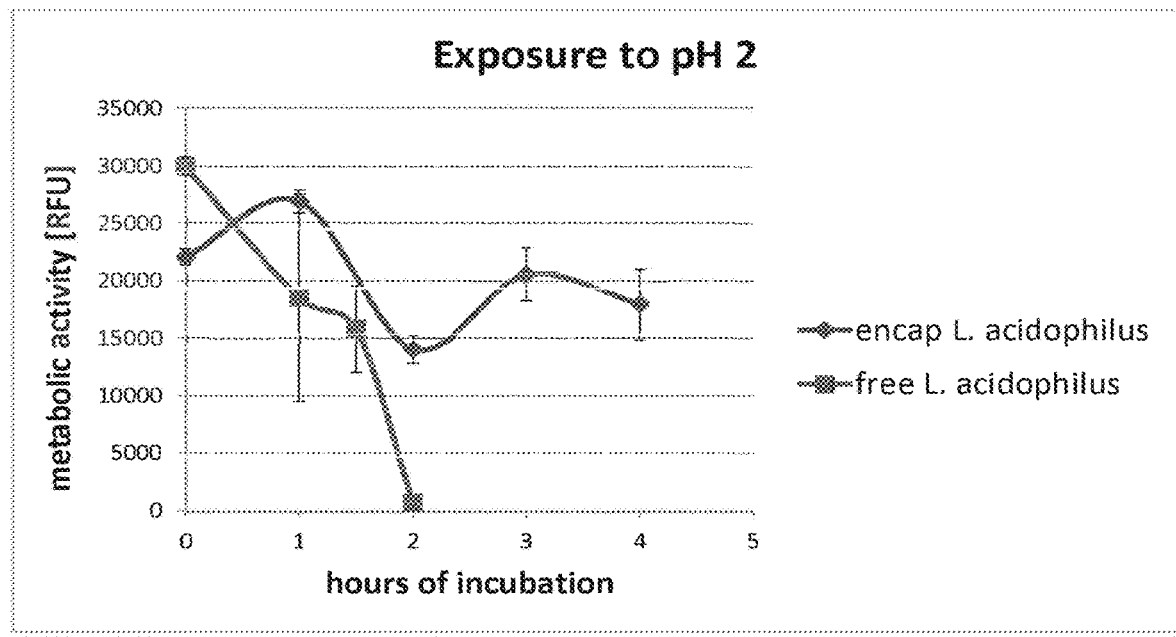
FIG. 4 shows the survival of free (squares) versus NaCS/pDADMAC encapsulated (rhombes) *Lactobacillus aci-*

The metabolically active encapsulated *lactobacillus* strain remains highly viable beyond 4 hours in the environment of hydrochloric acid salt solution, pH 2.0 while the non encapsulated *lactobacillus* bacteria do not survive beyond 1.5 hours in a hydrochloric acid salt solution environment at pH 2 (FIG. 4).

What is claimed is:

1. A method of supporting intestinal health of a subject having an unbalanced bacterial population in the intestine, comprising:
    administering a composition comprising encapsulated living bacterial cells to said subject, wherein the encapsulated living bacterial cells are encapsulated in microcapsules having a porous capsule wall, wherein the porous capsule wall comprises a complex formed from sodium cellulose sulphate and poly[dimethyldiallyl-ammonium chloride], wherein the microcapsules protect the living bacterial cells from being degraded by an acidic aqueous solution and the microcapsules release a majority of the living bacterial cells through pores in the capsule wall while passaging the intestine, and wherein the subject has an unbalanced microbial population in the intestine.

2. The method according to claim 1, wherein the subject is a human, pig, ruminant, cat, dog turkey, chicken, or goose.

3. The method according to claim 1, wherein 60% to 90% of the living bacterial cells remain viable.

4. The method according to claim 1, wherein at least 51% of the living bacterial cells remain viable.

5. The method according to claim 1, wherein the microcapsules have a diameter of between 0.01 and 5 mm.

6. The method according to claim 1, wherein surface pores of the porous capsule wall have a molecular weight cut off between 50 and 200 kDa.

7. The method according to claim 1, wherein the living bacterial cells for encapsulation are selected independently or as mixtures of living bacterial cells.

8. The method according to claim 7, wherein the living bacterial cells are *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Geobacillus*, or *Lactobacillus*.

9. The method according to claim 7, wherein the living bacterial cells are *Bacillus coagulans, Bacillus licheniformis, Bacillus subtilis, Bifidobacterium angulatum, Bifidobacterium animalis, Bifidobacterium bifidum, Bifidobacterium breve, Bifidobacterium infantis, Bifidobacterium lactis, Bifidobacterium longum, Enterococcus faecium, Enterococcus faecalis, Lactobacillus acidophilus, Lactobacillus amylovorus, Lactobacillus alimentarius, Lactobacillus bulgaricus, Lactobacillus casei* subsp. *casei, Lactobacillus casei Shirota, Lactobacillus curvatus, Lactobacillus delbrueckii* subsp. *lactis, Lactobacillus fermentum, Lactobacillus farciminus, Lactobacillus gasseri, Lactobacillus helveticus, Lactobacillus johnsonii, Lactobacillus lacti, Lactobacillus paracasei, Lactobacillus pentosaceus, Lactobacillus plantarum, Lactobacillus reuteri, Lactobacillus rhamnosus (Lactobacillus GG), Lactobacillus sake, Lactobacillus salivarius, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus*, or *Staphylococcus* xylosus.

10. The method according to claim 7, wherein the living bacterial cells are *Lactobacillus acidophilus, Lactobacillus caseei, Lactobacillus delbrueckii* subsp *bulgaricus, Lactobacillus johnsonii, Lactococcus lactis* subsp *lactis, Lactococcus lactis* subsp *cremoris, Streptococcus thermophilus, Bifidobacterium bifidum, Bifidobacterium angulatum*, or *Bifidobacterium longum*.

11. The method according to claim 1, wherein the encapsulated living bacterial cells are formulated in a food supplement or as a composition comprising a suitable carrier.

12. The method according to claim 1, wherein the living bacterial cells are encapsulated by microencapsulation comprising:

a) suspending living bacterial cells in an aqueous solution of a polyelectrolyte sodium cellulose sulphate;

b) introducing the suspension in the form of preformed microcapsules into a precipitation bath containing an aqueous solution of counter-charged polyelectrolyte poly[dimethyldiallyl-ammonium chloride];

c) incubating the living bacterial cells in the precipitation bath for a period of time ranging from 1-10 minutes; and d) harvesting the encapsulated living bacterial cells from the bath.

\* \* \* \* \*